(12) United States Patent
Hoerstrup et al.

(10) Patent No.: US 8,617,237 B2
(45) Date of Patent: *Dec. 31, 2013

(54) TUBULAR SUPPORTING PROSTHESIS WITH A HEART VALVE, IN PARTICULAR FOR AORTIC VALVE REPLACEMENT

(75) Inventors: Simon-Philipp Hoerstrup, Schweiz (CH); Gregor Zund, Schweiz (CH); Thilo Fliedner, Munich (DE); Frank Baaijens, Eindhoven (NL)

(73) Assignee: Universität Zürich, Zurich (CH)

( * ) Notice: Subject to any disclaimer, the term of this patent is extended or adjusted under 35 U.S.C. 154(b) by 166 days.

This patent is subject to a terminal disclaimer.

(21) Appl. No.: 12/527,138

(22) PCT Filed: Feb. 15, 2008

(86) PCT No.: PCT/EP2008/001173
§ 371 (c)(1),
(2), (4) Date: Jun. 14, 2010

(87) PCT Pub. No.: WO2008/098777
PCT Pub. Date: Aug. 21, 2008

(65) Prior Publication Data
US 2010/0280597 A1     Nov. 4, 2010

(30) Foreign Application Priority Data

Feb. 16, 2007  (EP) .................................... 07003350
Apr. 20, 2007  (EP) .................................... 07008151

(51) Int. Cl.
*A61F 2/24* (2006.01)
*A61F 2/06* (2013.01)
(52) U.S. Cl.
USPC ......... 623/2.14; 623/2.18; 623/1.2; 623/1.26; 623/1.46

(58) Field of Classification Search
USPC ................................ 623/2.14–2.19, 1.2, 1.26
See application file for complete search history.

(56) References Cited

U.S. PATENT DOCUMENTS

| 2004/0260389 A1* | 12/2004 | Case et al. | 623/1.24 |
| 2005/0245719 A1* | 11/2005 | Mather et al. | 528/60 |
| 2006/0122694 A1* | 6/2006 | Stinson et al. | 623/1.34 |

OTHER PUBLICATIONS

Breuer CK, Shin'oka T, Tanel RE, Zund G, Mooney DJ, Ma PX, Miura T, Colan S, Langer R, Mayer JE, Vacanti JP. Tissue engineering lamb heart valve leaflets. Biotechnol Bioeng. Jun. 5, 1996;50(5):562-7. Publ. Date: May 6, 1996.

Hill, Ronald J. et al., Quantitation of Types I and III Collagens in Human Tissue Samples and Cell Culture by Cyanogen Bromide Peptide Analysis, Analytical Biochemistry 141, 83-93 (1984).

(Continued)

*Primary Examiner* — Bruce E Snow
*Assistant Examiner* — Brian Dukert
(74) *Attorney, Agent, or Firm* — Sughrue Mion, PLLC

(57) ABSTRACT

The invention relates to a tubular supporting prosthesis, comprising two terminal regions relative to the longitudinal supporting prosthesis axis and a center region disposed between the two terminal regions, wherein every terminal region is provided with a mesh structure made of at least two structural rings, which are connected to each other via connecting members and are disposed point-symmetrically about the longitudinal supporting prosthesis axis. The center region is formed by elongated connecting members, which are connected to the structural rings respectively disposed adjacent to the center of the longitudinal supporting prosthesis axis. An aortic valve, which is produced by means of tissue engineering, is fastened and/or integrated in the center region.

27 Claims, 8 Drawing Sheets

(56) References Cited

OTHER PUBLICATIONS

Hoerstrup et al, Functional living Trileaflet, Functional Living Trileaflet Heart Valves Grown in Vitro Circulation 2000; 102;44-49; Publ. date Jul. 11, 2000.

Hoerstrup SP, Sodian R, Sperling JS, Vacanti JP, Mayer JE Jr. New pulsatile bioreactor for in vitro formation of tissue engineered heart valves. Tissue Eng. Feb. 2000; 6(1):75-9. Publ. Date: Jun. 2000.

Hoerstrup SP, Zünd G, Ye Q, Schoeberlein A, Schmid AC, Turina MI. Tissue engineering of a bioprosthetic heart valve: stimulation of extracellular matrix assessed by hydroxyproline assay. ASAIO J. Sep.-Oct. 1999;45(5):397-402. Publ. Date: Oct. 1999.

Hoerstrup, Simon P., et al, Functional Grown in Tissue-Engineered Living, Vascular Grats: Follow-Up at 100 Weeks in a Large Animal Model, Journal of American Heart Association; Circulations 2006; 114; 159-166.

Kanda K, Matsuda T. Behavior of arterial wall cells cultured on periodically stretched substrates. Cell Transplant. Nov.-Dec. 1993;2(6):475-84. Publ. Date: Nov. or Dec. 1993.

Mooney DJ, Breuer C, McNamara K, Vacanti JP, Langer R. Fabricating tubular devices from polymers of lactic and glycolic Acid for tissue engineering. Tissue Eng. 1995 Summer;1(2):107-18. Publ. Date: Feb. 1995.

Mooney DJ, Organ G, Vacanti JP, Langer R. Design and fabrication of biodegradable polymer devices to engineer tubular tissues. Cell Transplant. Mar.-Apr. 1994;3(2):203-10.Publ. Date: Mar. or Apr. 1994.

Shinoka T, Breuer CK, Tanel RE, Zund G, Miura T, Ma PX, Langer R, Vacanti JP, Mayer JE Jr. Tissue engineering heart valves: valve leaflet replacement study in a lamb model. Ann Thorac Surg. Dec. 1995;60(6 Suppl):S513-6. Publ. Date: Presentation Apr. 20-22, 1995 in Boston.

Shinoka T, Ma PX, Shum-Tim D, Breuer CK, Cusick RA, Zund G, Langer R, Vacanti JP, Mayer JE Jr. Tissue-engineered heart valves. Autologous valve leaflet replacement study in a lamb model. Circulation. Nov. 1, 1996;94(9 Suppl)II164-8 Publ. Date: Jan. 11, 1996.

Sodian, et al, Early in vivo experience with Tissue-Engineered Trileaflet Heart Valves, Circulation 2000; 102, 22-29; Publ. date Jul. 11, 2000.

Zünd et al; The in vitro construction of a tissue engineered bioprosthetic heart valve, European Journal of Cardio-Thoracic Surgery, 1997; 11:493-497; Publ. Date: Presented Sep. 24-27, 1995 in Paris.

Zünd G, Hoerstrup SP, Schoeberlein A, Lachat M, Uhlschmid G, Vogt PR, Turina M. Tissue engineering: a new approach in cardiovascular surgery: Seeding of human fibroblasts followed by human endothelial cells on resorbable mesh. Eur J Cardio-thoracic Surg. Feb. 1998;13(2):160-4. Publ. Date: Presented Sep. 28-Oct. 1, 1997.

\* cited by examiner

Fig. 2
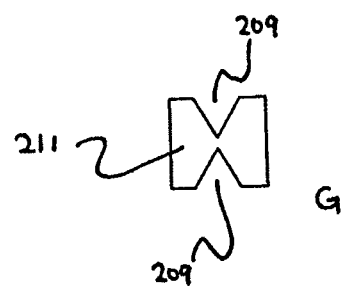
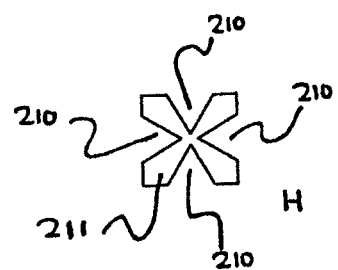

Fig. 7
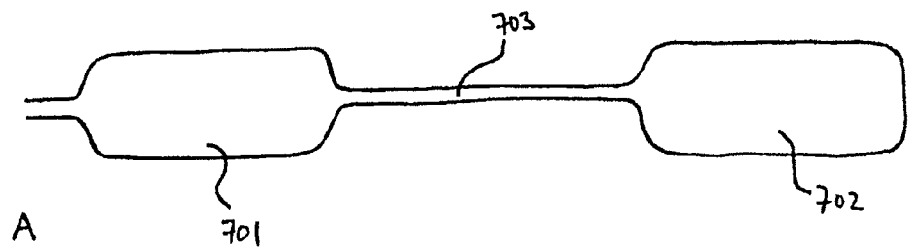
A
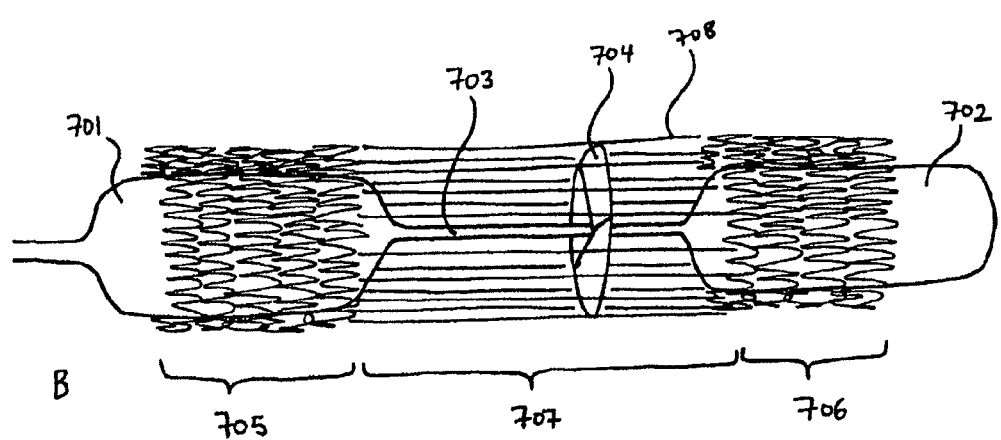
B
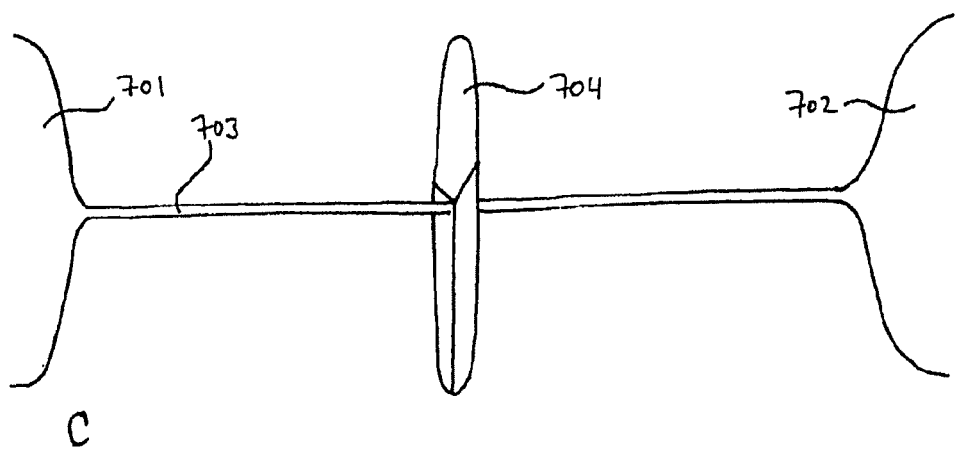
C

TUBULAR SUPPORTING PROSTHESIS WITH A HEART VALVE, IN PARTICULAR FOR AORTIC VALVE REPLACEMENT

The invention relates to supporting prostheses with heart valves. In particular, the invention relates to supporting prostheses with heart valves, in particular for aortic valve replacement.

BACKGROUND OF THE INVENTION

As a rule, valve prostheses are introduced into the body as an integrated part of vessel supporting prostheses. Such supporting prostheses are as a rule tubular lattice structures which are also referred to as "stents". Supporting prostheses with integrated valve replacement are known in the prior art. Such valves are obtained from cow, from pig as well as from horse. Supporting prostheses with tissue engineered ("TE") valves are also known (Stock et al. (2006). J. Thorac. Cardiovasc. Surg. 131, 1323-30). As compared to a xenograft, tissue engineering in general offers the advantage that cells of any desired origin (e.g. homologous or autologous human cells) can be integrated into the structure of an existing decellularized, non-human valve (see EP 1499366).

However, implanting such supporting prostheses with TE valves has proven to be extremely difficult in practice, since TE valves as a rule are very sensitive. For instance, when they are introduced into the body inside a supporting prosthesis made of for example metal, such valves can be ripped or crushed by this supporting prosthesis and/or become caught within the supporting prosthesis. This leads to undesirable damage of the valve disposed in the stent. In a TE valve damaged in this way, degeneration and/or malfunction of the valve can result.

In the prior art, this problem has been solved by lining the inside of a valve-containing stent with xenograft tissue. For instance, a mucosa layer from the pig small intestine was sutured to the inside of a metal stent. Subsequently, a pulmonary valve was connected with this mucosal layer. The mucosal layer served as a sort of shield against the metal structure of the stent which could potentially damage the valve (Stock et al. (2006). J. Thorac. Cardiovasc. Surg. 131, 1323-30.) It has been determined that the heart valve in such a stent lined on its inside with tissue was less severely damaged than valves in stents which comprised no tissue layer of any sort, or a tissue layer only on the outside.

Nevertheless, such prostheses lined on their inside with tissue layers are associated with significant disadvantages. First, the preparation for implantation is complicated by the necessity of attaching an additional layer on the inside of the stent. Second, the use of tissue layers of non-human origin implies significant risks with regard to an infection and/or transplant rejection in the human patient. On the other hand, it would be difficult to isolate sufficient quantities of autologous mucosal layer for lining the stent to be introduced from every patient needing a valve prosthesis.

Independent of these disadvantages in known stents containing a replacement valve, significant difficulties exist in the special context of the aortic valve prostheses. These difficulties result partially from the general sensitivity of valve prostheses as explained above, but also from the anatomical particularities in he aorta region in particular. Due the high blood pressure in the aorta region, the aorta tissue is subjected to exceptional physical strains. In order to withstand these strains while still fulfilling its supporting functions, a stent intended for the aorta region must therefore be robust, wherein a rigidity in the stent structure may mean a great danger of damage for the valve located therein. Further, the introduction of a very robust stent in the region of the aorta brings with it the danger that other vessels important for life, such as for example the coronary arteries ostium dextra and ostium sinistra descending on both sides of the aorta are disrupted in their function.

It is thus an aim of the present invention to provide an improved stent with valve replacement which enables the implantation of a sensitive TE valve in regions of great strain such as in the aorta, where in the disadvantages mentioned above are avoided.

SUMMARY OF THE INVENTION

According to the invention, this problem is solved by the provision of a tubular supporting prosthesis comprising two terminal regions relative to the longitudinal axis of the supporting prosthesis and a middle region disposed between the two terminal region wherein each terminal region comprises a mesh structure made of at least two structural rings which are connected with one another via connecting members and are disposed point symmetrically about the longitudinal axis of the supporting prosthesis, wherein the middle region is formed by elongated connecting members which are connected with each of the structural rings disposed closest to the middle point of the longitudinal axis of the supporting prosthesis, and wherein an aortic valve produced by means of tissue engineering is fixed and/or integrated into the middle region.

Such a supporting prosthesis construction offers several surprising advantages.

First, the aortic valve is disposed in the middle region, i.e. it is not primarily connected with the proximal or with the distal mesh structure. In the supporting prosthesis according to the invention the two terminal mesh structures are the regions of highest robustness, i.e. rigidity, whereas the middle region formed by the elongated connecting members is by comparison less rigid. By attaching the sensitive TE aortic valve to this comparatively less rigid middle region, potentially damaging interactions between the aortic valve and the terminal mesh structures are avoided to a large extent.

Second, by fixing the position of the aortic valve in the middle region of the supporting prosthesis, the damage to the valve which is typically caused by expanding the supporting prosthesis by means of a balloon catheter during the implantation procedure is avoided. In this way, the supporting prosthesis according to the invention can be introduced at the correct position in the body with the help of a two-part balloon catheter, wherein the one part of the balloon catheter blows up the mesh structure in the first terminal region of the supporting prosthesis and the second part of the balloon catheter blows up the mesh structure in the second terminal region of the supporting prosthesis. In the middle region of the supporting prosthesis, i.e. in the region in which the TE aortic valve is located, no balloon expansion takes place during insertion and expansion of the terminal regions of the supporting prosthesis, i.e. the balloon is not expandable or is only difficultly expandable in its middle region, so that the aortic valve is not pressed against the surrounding prosthesis structure. In this way the supporting prosthesis according to the invention allows an anchoring in the aorta and/or in the left ventricular efflux tracht, without damaging the sensitive TE aortic valve located within the supporting prosthesis.

Third, the elongated connecting members in the middle region of the supporting prosthesis render this region significantly looser than both of the terminal regions of the supporting prosthesis comprising both of the mesh structures. In this way, an additional problem which commonly arises in aortic valve replacement is avoided, namely the disruption of the coronary arteries ostrium dextra and ostrium sinistra branching out from the aorta. The supporting prosthesis according to the invention can thus be introduced into the body of the patient such that the loose middle region of the supporting prosthesis is at the same height as both of these branching coronary arteries, whereby a disruption or even an occlusion of these arteries important for life is advantageously excluded.

According to one embodiment of the present invention, at least one mesh structure comprising n periodic deformations which extend along the longitudinal axis of the supporting prosthesis and form crests and troughs, said deformations comprising an amplitude A in relation to the longitudinal axis of the supporting prosthesis, wherein n=16-70, preferred 20-56 especially preferred 24-42. Here, A is to be understood as the maximal deflection of a respective deformation from its middle position, that is away from a circumferential middle line M defined for each structural ring (wherein M includes a surface which perpendicularly intersects the longitudinal axis of the supporting prosthesis), and is 0.25-8 mm, preferred 0.75-4 mm, especially preferred 1-2 mm. These deformations, which can be of an sinusoidal, rectangular, saw tooth, triangular or meandering in shape, preferably of sinusoidal shape, confer on the terminal regions of the supporting prosthesis their foldabililty and elasticity necessary for the insertion by means of catheter, i.e. allow that the terminal regions of the supporting prosthesis prior to insertion into a patient can be reduced to the required diameter without being significantly shortened in their total length.

According to a further embodiment, each terminal mesh structure comprises 2-8, preferred 2-6, especially preferred 2-4 structural rings.

According to a further embodiment of the present invention, the number of the periodic deformation of two respectively neighboring structural rings is identical, or the number of the periodic deformations differs from one another by a multiple whole number. If the number of deformations of respectively neighboring structural rings in the terminal regions is identical, then every deformation of a structural ring can be connected with every, or for example with every second, third or fourth corresponding deformation of a respectively neighboring structural ring via the connecting members in order to form the terminal mesh structure. This has the advantage that a supporting prosthesis with a very regular mesh structure is formed which supports the inner wall of the aorta with the same force at every point over the entire length of the respective mesh structure. If the number of periodic deformations of two respectively neighboring structural rings differs from one another by a multiple whole number, then every deformation of one structural ring can be connected with every second, every third, every fourth etc. deformation of a respectively neighboring structural ring in respective terminal region of the supporting prosthesis via connecting members. In this way, the density of the mesh structure over the length of a respective terminal region can be designed differently in order to fulfill different clinical requirements in which different supporting forces are required along a supported segment of the aorta. It is possible here to adjust the rigidity of the respective terminal region mesh structures independently of one another. Each terminal region of the supporting prosthesis according to this embodiment of the invention can be designed in such a way that, by suitable choice of the number of periodic deformations of respectively neighboring structural rings, the radial supporting force of the respective mesh structure along the entire length of the respective terminal region can continually decrease or increase. According to this embodiment of the invention, designs are also conceivable in which the radial supporting force of a respective mesh structure decreases toward the middle of the mesh structure, i.e. this supporting force is greater at both ends of a respective mesh structure than in the middle of this mesh structure. Conversely, other designs are possible in which the density of a respective mesh structure is chosen by suitable choice of a number of the periodic deformations of respectively neighboring structural rings such that the supporting force is greatest in the middle of a respective terminal mesh structure.

According to a further embodiment, the supporting prosthesis can further contain at least one holding device in order to prevent undesirable slipping within the vessel following implantation. The at least one holding device can for example be designed as a hook and eye, an anchoring in the natural valve-ring structure (called the aorta valve annulus) to the aortic wall with folding legs and/or an hourglass formation of one end of the supporting prosthesis.

According to a further embodiment of the present invention, two neighboring structural rings are disposed with respect to one another in phase-shifted manner, such that crests of the one structural ring can be connected via the connecting members with troughs of a respectively neighboring structural ring. In many of the vessel supporting prostheses known in the prior art, two neighboring periodically deformed rings of the prosthesis structure are connected via their respective crests or troughs so that the crest of one ring is connected with the crest of a respectively neighboring ring, or the trough of a one ring is connected with the trough of a respectively neighboring ring. If however two neighboring structural rings are point-symmetrically rotated against one another about the longitudinal axis of the supporting prosthesis such that the crest of one deformed structural ring lies opposite the trough of a respectively neighboring deformed ring, then the crest of the one ring can be connected with the trough of the respective neighboring ring via a connecting member, whereby a very high flexibility of the respective terminal mesh structures can be achieved. According to a further embodiment, it is possible to connect a crest of one structural ring with a middle point, i.e. with a point on or next to the middle line M as defined above of the respectively neighboring structural ring. According to a further embodiment it is possible to connect a middle point, i.e. a point on or next to the middle line M of one structural ring with a middle point of a respectively neighboring structural ring. According to a further embodiment it is possible to connect a trough of one structural ring with the middle point, i.e. a point on or next to the middle line M of a respectively neighboring structural ring.

The supporting prosthesis containing the aortic valve can be easily compressed to the required diameter prior to insertion, especially with a crest-trough connection, without losing any of its advantageous support capacity in both of the terminal regions comprising the mesh structure. In this regard the connection between respectively neighboring mesh structures can be designed as rings, clamps or loops, threads, wires or struts, said loops, threads, wires or struts extending parallel to the main axis of the supporting prosthesis (also called "longitudinal axis of the supporting prosthesis"). Designing the connecting members as struts is especially advantageous. In this regard, it is also advantageous to design the elongated connecting members of the middle region of the supporting prosthesis as struts which are connected to the two structural rings neighboring the middle region.

The connecting members can be loosely or rigidly connected to the respectively neighboring structural rings. By a loose connection, for example by means of polymers or metals which are softer than the basis material of the supporting prosthesis, one can achieve a very high flexibility in both of the terminal regions comprising the mesh structure. Such a loose connection of the structural rings can also be effected by means of wire, a clip or suture material. At least one predetermined breaking point can also be provided on the respective connecting members.

In contrast, a rigid connection of the connecting members to their respective structural rings has a stiffening effect on the mesh structure. The connecting members which connect two respectively neighboring structural rings with one another are preferably fashioned as rigid struts which are preferably seamlessly integrated into the structure of the respectively neighboring structural rings. In the case that the supporting prosthesis capable of growth is to be cut out of a tubular blank, for example by means of a laser, such rigid struts or bridges can be fashioned in a simple manner known to the skilled person such that the blank is not cut at the positions where connecting members are later to be provided.

It is also conceivable that in one segment of the supporting prosthesis loose connection members are used, whereas in another segment of the supporting prosthesis rigid connection members are used. A mixture of loose and rigid connection members over the entire structure of a respective terminal mesh structure is also conceivable. In general, the respective terminal mesh structures can be designed independently of one another.

According to a further embodiment of the present invention, the structural rings and/or the connecting members are made at least in part of biologically degradable material such as for example at least one metal and/or at least on polymer. In this way and as dependent on need, it can be ensured that at least a part of the structure of the supporting prosthesis dissolves with time, wherein the TE aorta valve grows together with the aortal wall in an advantageous manner. According to the present embodiment, the surrounding structure of the prosthesis can be made completely or in part of biologically degradable material. If the supporting prosthesis is made completely of biologically degradable material, the prosthesis structure dissolves completely after some time, wherein only the aortic valve originally present in the supporting prosthesis remains. If the supporting prosthesis is made only in part out of biologically degradable material, the biologically degradable material disappears sometime following the implantation, wherein fragments of the supporting prosthesis which are not made of biologically degradable material remain and assume the long term supporting function. It is thus conceivable that the entire structure of the supporting prosthesis surrounding the aortic valve is not made of biologically degradable material, so that the aortic valve prosthesis serves as a permanent prosthesis. The choice of the materials, i.e. whether the supporting prosthesis according to the invention is composed completely, partially or not at all of biologically degradable material, depends as a rule on the patient to be treated. However, it can generally be said that in cases of an increased need of supporting function, designs with higher proportions of non-biologically degradable material are to be preferred, since such supporting prostheses are able to impart a high radial supporting force.

According to a further embodiment of the present invention, the biologically degradable material is made of at least one alloy, at least one polymer or at least one stainless steel with shape memory. It is especially preferred that the alloy with shape memory is a nickel-titanium alloy such as for example the known nitinol, an aluminum alloy, a magnesium alloy or an iron alloy. Suitable polymers with shape memory are for example tert-butylacrylate or poly(ethyleneglycol) dimethylacrylate or PCL combined with 2,4-toluenediisocyanate ethylenglycol.

Suitable biologically degradable polymers are primarily polyglycolic acids (PGA), polylactic acid (PLA), polyhydroxyalkanoate (PHA) and poly-4-hydroxybutyrate (P4HB), polycaprolactones (PLGA), polycarbonates, polyamides, polyanhydrides, polyamino acids, polyorthoesters, polyacetates, polycyanoacrylates as well as degradable polyurethanes and non-erodable polymers such as polyacrylates, ethylenevinylacetate polymers and other substituted cellulose acetates as well as derivates thereof. Polyesters are preferred. Preferred biologically degradable polymers include polymers of the following groups: polyesters of the hydroxycarboxy acids, polyanhydrides of the dicarboxyesters and copolymers of the hydroxycarboxy acids and of the dicarboxyesters.

In a further embodiment the material is composed of a synthetic polymer made of at least one of the following monomers: glycolide, lactide, p-dioaxonon, caprolactone, trimethylenecarbonate butyrolactone. In special embodiments, the material is chosen from a group consisting of polymers or copolymers of glycolic acid, lactic acid and sebacic acid. Polyglycolic acid polymers are preferred.

These polymers can be used both in pure form as well as in mixtures of two or more of the named substances or mixtures of these substances with further biologically degradable polymers. In a preferred embodiment a mixed polymer made of 80-98% PGA and 20-2% PHA is used.

In a further special embodiment the biologically degradable material includes a polyhydroxyalkanoate (PHA). PHA can be coated with a further non-degradable polymer or can itself serve as a coating. A preferred polyhydroxyalkanoate for this use degrades in vivo within less than 9 months, more preferred within less than 6 months and most preferred within less than 3 months. A preferred composition of the polyhydroxyalkanoates contains 2-, 3-, 4- or 5-hydroxy acids, for example poly-4-hydroxybutyrates. The composition can further contain a poly-4hydroxybutyrate-co-3-hydroxybutyrate as well as combinations thereof. Most preferred is poly-4-hydroxybutyrate.

In a further special embodiment the biologically degradable material includes homopolymers and copolymers with any desired combination of the following monomers: 3-hydroxybutyrates, 3-hydroxyvalerate, 3-hydroxypropionate, 2-hydroxybutyrate, 4-hydroxybutyrate, 4-hydroxyvalerate, 3-hydroxyhexanoate, 3-hydroxyheptanoate, 3-hydroxyoctanoate, 3-hydroxynonanoate, 3-hydroxytridecanoate, 3-hydroxytetradecanoate, 3-hydroxypentadecanoate, 3-hydroxyhexadecanoate, 3-hydroxyheptadecanoate and 3-hydroxyoctadecanoate.

According to a further embodiment of the invention the supporting prosthesis can be made of non-biologically degradable material and can be coated with one or more biologically degradable materials, e.g. polymers. Further it is also possible, according to a further embodiment of the invention, that the supporting prosthesis is made of a biologically degradable material and is coated with one or more non-biologically degradable materials.

Both the biologically degradable material as well as the non-biologically degradable material can be a polymer or a metal.

Suitable non- or only difficultly biologically degradable materials are carbon, PTFE dacron, PHA or poly-3-hydroxybutyrate (P3HB).

According to a further embodiment of the present invention, the structural rings and/or connecting members comprise at least one predetermined breaking point.

The term "predetermined breaking point" is generally to be understood such that at this position in the structural ring and/or in the connecting member it is not only possible that the predetermined breaking point is broken, or i forced apart, or broken apart, but also possible that the predetermined breaking point is stretched. A stretching of the predetermined breaking point is to be seen as a plastic deformation of this, in which the geometry of the predetermined breaking point changes without the parts of the supporting prosthesis neighboring the predetermined breaking point necessarily becoming separated. The stretching of a predetermined breaking point can occur as a preliminary stage of the final breaking of the predetermined breaking point. As such, interpretations of a predetermined breaking point on the one hand as a breaking point and on the other hand as stretching point do not mutually exclude one another. Although the predetermined breaking point will be spoken of in the following text primarily as a breaking point, it is clear to the skilled person that, depending on the conditions, a stretching point may (also) be understood.

Provision of predetermined breaking points allows a long-term growth of the supporting prosthesis without a significant reduction in the desired supporting function. The supporting prosthesis with an aortic valve according to this embodiment may be populated, prior to implantation in the patient, with homologous, preferably with autologous cells, preferably endothelial cells, fibroblasts and/or myofibroblasts and/or further progenitor cells and/or stem cells, or may be supplemented with tissue already produced in vitro. The supporting prosthesis populated in this way is compressed ("crimped") to the required size or to the required diameter and the supporting prosthesis compressed in this way is for example introduced to the desired location in the body via a vein catheter. In this way, the supporting prosthesis can serve its supporting function in the vessel following possibly necessary expansion by means of special two-part balloon catheter as set out above, without damaging the sensitive TE aortic valve. If the vessel such as for example that of a small child becomes larger with time, the supporting prosthesis can grow with the vessel. By incorporation of, preferably, homologous cells into the supporting prosthesis and/or into the aortic valve, it is ensured that the growth rate of the supporting prosthesis is substantially identical to that of the vessel. With increased lumen of the vessel, forces act upon the supporting prosthesis which can lead to pointwise breaks at the predetermined breaking points in both of the terminal mesh structures, i.e. the terminal mesh structures of the supporting prosthesis can be forced apart at their predetermined breaking points by the radial forces arising from growth. In this way, according to this embodiment of this invention, the supporting prosthesis together with the heart valve disposed therein can automatically adapt to a vessel lumen circumference which has become larger, wherein an adequate supporting function is still ensured by the interaction of the cell tissue populating the supporting prosthesis and the remaining fragments of the terminal mesh structure.

It is possible to design the predetermined breaking points e.g. in the terminal mesh structures such that these dissolve with time, in order to allow a forcing apart or a breaking apart at the weak points generated due to the growth process (passive forcing apart). An active forcing apart of the predetermined breaking points is also conceivable, for example by means of balloon angioplasty, in order to adapt an already implanted supporting prosthesis to a lumen which has become larger since implantation.

The at least one predetermined breaking point can also be designed such that it is forced apart, dissolved or weakened by external influence. Such a design of the predetermined breaking points has the particular advantage that the forcing apart of a supporting prosthesis which is, for example, already implanted in the early childhood years can later be effected or at least promoted from outside, without the child who has since grown needing to undergo another operation. The external influence can be chosen from sound waves; at least one magnetic field; a combination of magnetic field and electromagnetic field; electromagnetic radiation; electrical energy and any desired combination thereof. The external influence can be applied from inside or outside the body; it is applied at least from outside the supporting prosthesis. In the case that the external influence is applied from inside the body, it can for example be applied with the help of an intravascular catheter or in a minimally invasive manner with the help of endoscopy. The sound waves can for example be ultrasound and/or shock waves. The combination of magnetic field and electromagnetic field can for example be magnetic resonance imaging (MRI). The electromagnetic radiation can for example be X-ray radiation or infrared radiation (thermal energy). For example a steep decrease in the stiffness of a predetermined breaking point (stretching of the predetermined breaking point by plastic deformation) or even a break of the predetermined breaking point can be achieved by means of a local increase in temperature.

Independently of whether the supporting prosthesis is actively or passively forced apart, the predetermined breaking points of the supporting prosthesis according to the invention allow the size, e.g. the diameter of the supporting prosthesis according to the invention to be adapted to the diameter of the vessel without damaging the flaps of the TE aortic valve.

The concrete design of the predetermined breaking points is not restricted as long as they can exert their function as described above. In a concrete sense, this function can be realized in different manners. In a supporting prosthesis made of a metallic material, a predetermined breaking point can for example be designed as at least one perforation in a strut of a structural ring or in the connecting member. Such perforations can take different forms, for example as one or more piercing holes and/or as one or more non-piercing cavities in the supporting prosthesis material. The shape of the holes or of the cavities is not restricted: it can be round, elliptical, polygonal, rectangular and/or quadratic. The cavity can also be designed as a notch in the material of the supporting prosthesis, which for example extends perpendicularly or diagonally over the width of a structural ring and or of a connecting member. It is also possible to dispose such notches or narrowings on both sides of a strut of a structural ring and/or of a connecting member, such that two notches form the predetermined breaking point from both sides of the structural ring or of the connecting member (i.e. from above and below), that is from the sides of the supporting prosthesis facing the vessel wall as well as the vessel lumen. Alternatively or also supplementary thereto, one or two notches can be disposed right and left at the same location, i.e. at the same height of the strut as the two notches disposed above and below. In this way, the strength of a predetermined breaking point can be adjusted by making it out of one, two, three or four notches which are all disposed at the same height of the strut or of the connecting member. Although this embodiment assumes a strut and/or a connecting member with a four-sided cross section, it is to be noted that corresponding considerations apply for struts and/or connecting members with differently designed cross sections.

Depending on the concrete physiological requirements, it is also conceivable that at least one predetermined breaking point is made in at least one elongated connecting member in order to allow or promote growth along the longitudinal axis of the supporting prosthesis.

It is also possible to design a predetermined breaking point to exceed the plastic deformability of a strut of the structural ring in a point-wise or linear manner and/or to create point-wise or linear differences in the structural density of the support prosthesis material. Predetermined breaking points can also be effected by creating point-wise or linear damage to the surface structure or to the inner structure of the structural ring and/or to the connecting member for example by increasing the porosity of the material at a particular position, for example by incorporating nanoparticles it the region of the predetermined breaking point). A positionally restricted or unrestricted mixture of the basis material of the supporting prosthesis with polymer and/or polymer interponates, wires, threads and/or organic interponates such as for example collagen is also conceivable.

A predetermined breaking point can also be designed as a cut or a gap in the material of the supporting prosthesis (i.e. in the structural ring or in the connecting member). This cut or gap can be covered with a non-metallic material, for example with a biologically degradable material in the region of the predetermined breaking point so that, at first, only the biologically degradable material holds the predetermined breaking point together. This can for example be achieved in that the biologically degradable material overlaps on both sides of the cut or the gap on the material of the structural ring or the connecting member and is connected to this. If the biologically degradable material dissolves in the body over time, its holding capacity is correspondingly reduced until either the destructive forces generated due to the growth exceed the holding capacity of the biologically degradable material, or the biologically degradable material completely dissolves and exposes the cut or the gap lying thereunder, so that the supporting prosthesis can grow unhindered (or can be expanded open by the means of balloon angioplasty). The rate of the growth process can be controlled by suitable choice of the biologically degradable material used at the predetermined breaking point, as it is known that different biologically degradable materials dissolve in vivo at different rates.

As mentioned above, the at least one predetermined breaking point can be designed such that it can be forced apart dissolved or weakened by external influence.

Since the amount of the biologically degradable material at the predetermined breaking points is as a rule very low, one need not fear any inflammatory reaction due to its dissolution, as is the case in the prior art with the dissolution of supporting prostheses which are made completely of biologically degradable material.

A corresponding design using a biologically degradable material is also possible in the case that, instead of a cut or a gap, a perforation and/or a notch in the material of the supporting prosthesis is provided as described above.

It is also possible, independently of the design as a perforation, notch, cavity, gap or cut at the at least one predetermined breaking point, to apply multiple layers of different biologically degradable materials, so that the supporting prosthesis can be forced apart in a chronologically graduated manner. In this way, it can for example be ensured that the dissolution of the predetermined breaking point initially proceeds very slowly and, only after longer time (that is after the slowly dissolving outer layer has disappeared), the rate of dissolution of the predetermined breaking point and the associated growth potential of the supporting prosthesis increases, or vice versa.

It is also possible that a supporting prosthesis comprises differently designed predetermined breaking points. For example, a supporting prosthesis can comprise one or more predetermined breaking points as perforations without biologically degradable material and one or more predetermined breaking points as cuts and/or gaps covered with one or more biologically degradable materials. In this way, it can be ensured that different regions of the supporting prosthesis grow at different rates in vivo within the same amount of time. The supporting prosthesis according to the invention thus allows a very high degree of flexibility in the adaption to the most diverse physical requirements.

It is also possible to use a non-biologically degradable polymer in the region of the predetermined breaking points. The predetermined breaking point can be designed as described above, e.g. as a perforation, notch, cavity, gap or cut. In the case that non-biologically degradable polymer is applied in an overlapping fashion on both sides over a cut or a gap in the structural ring and/or in the connecting member, then the strength in the predetermined breaking point and thus also the growth capacity of the supporting prosthesis depends on the strength of the non-biologically degradable polymer. By knowing the material strength of the non-biologically degradable polymer, the strength or the growth characteristics of the supporting prosthesis can in this way be controlled depending on physiological requirements.

It is also possible to provide at least one predetermined breaking point as set out above in or on at least one of the elongated connecting members of the middle region as well as on at least one connecting point of at least one elongated connecting member with the structural ring facing it. According to a further embodiment of the present invention, the at least one predetermined breaking point is preferably disposed on or next to the middle point between a crest and a trough of the periodically deformed structural ring of at least one terminal region, that is on or next to the intersection point of the structural ring with the middle line M as defined above. Additionally or alternatively thereto, the at least one predetermined breaking point can however also be disposed on the crests and/or troughs of the periodic deformations of the structural ring. As the support prosthesis grows or is forced apart in the manner described above, radial forces extending from inside to outside are exerted on both of the terminal regions the supporting prosthesis. In the case that the supporting prosthesis is expanded open during the process of growth and/or angioplasty, these forces concentrate at the crests and troughs of the structural rings, since these crests and troughs of the terminal mesh structures of the supporting prosthesis confer a large part of its flexional capacity. If the predetermined breaking points are disposed exclusively on the crests and troughs of the periodically deformable structural ring, there exists the danger that the total mesh structure will be prematurely forced apart, whereby in some cases a large part of its supporting function would be undesirably lost. However, if the predetermined breaking points are exclusively or predominantly disposed on or next to the middle point between the crests and the troughs of the periodically deformable structural ring, in some cases the breaking apart of the mesh structure may be delayed.

By the targeted mixing of the positions on which the predetermined breaking points are disposed, the tendency of the supporting prosthesis to be forced apart can be controlled in a very advantageous manner. The more predetermined breaking points are disposed on crests and/or troughs of a periodically deformable structural ring, the greater is the tendency of the respective terminal mesh structure to be forced apart. The more predetermined breaking points are disposed on or next to the middle points of a periodically deformable structural ring, the less is the tendency of the respective terminal mesh structure to be forced apart.

According to a preferred embodiment, the predetermined breaking points comprise or consist of a non-metallic material, for example a polymer material. This material can be a polymer and can be biologically degradable or non-biologically degradable. Such an embodiment implies certain advantages.

First, as a rule, polymer materials have a lower tensile strength than metallic materials wherein the tensile strength depends directly on the degree of degradation of the material used. In the growth-capable supporting prosthesis with an aortic valve according to the present embodiment, a higher tensile strength at the predetermined breaking points would have a growth inhibiting effect, since the predetermined breaking points can only difficultly be ripped apart from one another. Conversely, the growth capability of the supporting prosthesis can be promoted by the choice of a material with a higher ripping tendency at the predetermined breaking points. In this way, by using a non-metallic material of a known tensile strength at the predetermined breaking points, one has the possibility to provide supporting prostheses of different growth abilities. In this way, the growth ability of the supporting prosthesis provided can be adapted to the specific clinical requirements of any patient.

Secondly, by designing the predetermined breaking points with non-metallic material, it can be ensured that, following the breaking apart of the terminal mesh structures due to growth or expansion, no sharp edged corners of metal are formed which can later injure the supported vessel wall or which can break off and disrupt a distant location in the vessel system.

For the case that the mesh structure of the supporting prosthesis consists of a metallic material and the predetermined breaking points consist of or comprise a non-metallic material, the non-metallic material is preferably applied in the region of the predetermined breaking points by coating on to the metallic material of the supporting prosthesis. Here, the metallic material of the mesh structure preferably comprises a polished surface structure of a rounded shape, at least in the region of the predetermined breaking points, i.e. underneath the coating of non-metallic material. In this way it is endured that the even after the breaking apart of the predetermined breaking points and, the case may be, after the dissolution of the non-metallic material, a smooth surface of the mesh structures or no sharp edges on these predetermined breaking points remain, whereby the mentioned advantage of the reduced risk of injury is realized. Methods for polishing metallic fine structures such as for example electropolishing are known to the skilled person.

According to a further embodiment of the invention, the predetermined breaking point can be designed such that its rigidity or holding ability decreases only after a strain of predetermined duration or of predetermined magnitude. For example, the predetermined breaking point of a supporting prosthesis capable of growth which is intended for the aorta region can be fashioned such that the threshold value of the maximal tolerated mechanical strain of the material of the predetermined breaking point is only reached after a determined number of heartbeats, said strain being caused by pumping of the heart. Assuming an average heart rate, one can thus effectively pre-program the duration following implantation after which the supporting prosthesis begins to dissolve or to expand. This allows a control of the growth rate of the supporting prosthesis which is particularly advantageous for the use in small children, since by this, the number of surgical interventions can be significantly reduced. It is also conceivable that the strain to which the predetermined breaking point is to be subjected is of a non-mechanical nature. According to a further embodiment of the present invention, the length of the elongated connecting members is 0.75 to 3-fold of the amplitude A. The length of the elongated connecting members of the middle region of the supporting prosthesis is preferably 1 to 2-fold of the amplitude A. By adjusting the length of the elongated connecting members in the middle region of the supporting prosthesis, one can advantageously adapt to different anatomical requirements, i.e. one can shorten or lengthen the middle region of the supporting prosthesis depending on the anatomical requirements in the region into which the supporting prosthesis is to be introduced.

The TE aortic valve can advantageously be sewed, glued, clamped or woven to the middle region of the supporting prosthesis, wherein it is preferred to sew the TE aortic valve to the middle region of the supporting prosthesis. Ideally, the TE aortic valve is to be attached at a height of the middle region such that, following implantation, the supporting prosthesis according to the invention resides at its native position, i.e. at the position where the body's own aortic valve previously resided. Preferably, the aortic valve lies in the distal half of the middle region of the supporting prosthesis, i.e. in the half of the supporting prosthesis which, in the implanted state is closer to the heart.

BRIEF DESCRIPTION OF THE SEVERAL VIEWS OF THE DRAWINGS

The following figures and examples illustrate the invention in non-limiting fashion. The figures show:

FIG. 7A: A special angioplasty balloon suitable for expansion of a supporting prosthesis according to the invention. The balloon is shown in its fully expanded state. The balloon consists essentially of three regions: a proximal expandable region (701); a middle non- or only slightly expandable region (703); and a distal expandable region (702).

FIG. 7B: A perspective view of the special angioplasty balloon from FIG. 7A. The use of the special balloon for expanding an embodiment of the supporting prosthesis according to the invention is depicted. First, the special, not yet expanded balloon is inserted in a supporting prosthesis such that the height of the proximal expandable region (701), of the middle region (703) and the distal expandable region (702) correspond approximately to the respective heights of the terminal region (705), the middle region (707) including the TE aortic valve (704) and the terminal region (706) of the supporting prosthesis. Here, care should be taken that the aortic valve (704) is located at the height of the middle region (703) of the balloon. If the balloon inserted in this manner is then expanded the terminal regions (705, 706) of the supporting prosthesis comprising a mesh structure are expanded, however the middle region (707) where the aorta valve (704) is disposed as fixed to the elongated connecting members (708) is not. In this way, it is avoided that in expanding the balloon the sensitive flaps of the TE aortic valve are damaged.

FIG. 7C: A detailed view of the interaction between the middle region (703) of the balloon and the TE aortic valve (704). The balloon is depicted in its fully expanded state as can be seen in the proximal (701) as well as distal (702) expandable regions. Not shown are the remaining parts of the supporting prosthesis containing the TE aortic valve. As can be seen from the drawing, the middle balloon region (703) still remains very thin even in the fully expanded state so that it can pass through the middle of the aortic valve without damaging the surrounding valve flaps.

DETAILED DESCRIPTION OF THE INVENTION

The following example explains in a non-limiting manner how the supporting prosthesis capable of growth can be prepared.

Example 1

Manufacture of a Supporting Prosthesis Carrying a Valve

Figure 1:
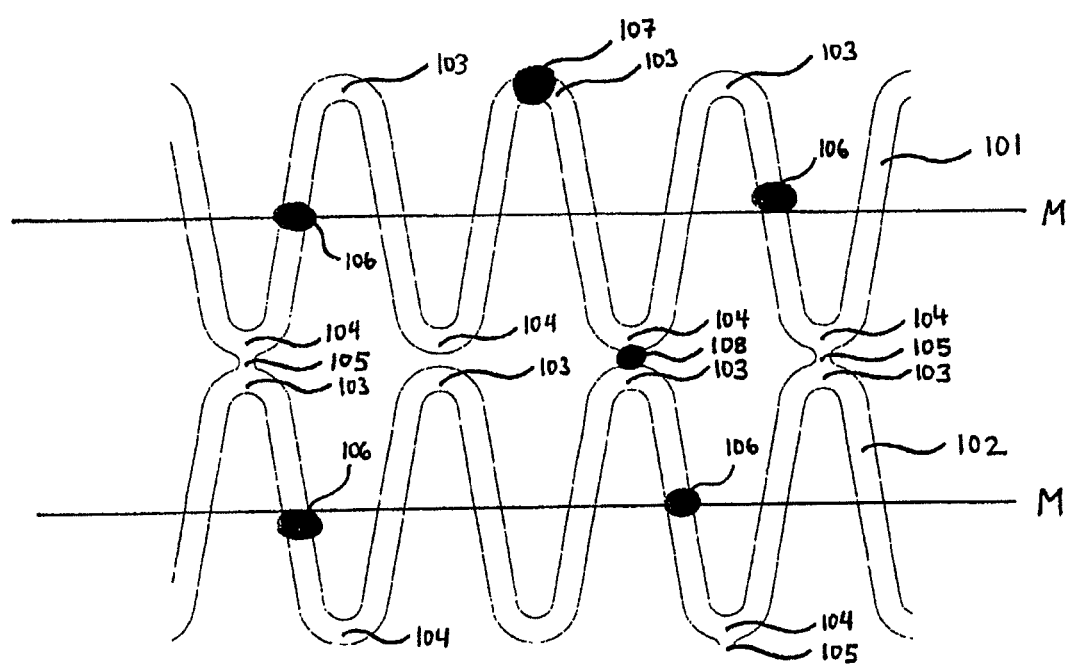
FIG. 1: A plan view of a segment of the mesh structure in an terminal region of a supporting prosthesis according to one embodiment of the invention. The following are depicted: a first periodically deformed structural ring (101) and a second periodically deformed structural ring (102), each with crests (103) and troughs (104) which in their middle define the circumferential middle line M. The first and second structural ring (101 and 102) are connected with one another via connecting members (105) fashioned as struts. Here, the mesh region depicted comprises predetermined breaking points. These are depicted as black dots which are disposed in the embodiment shown on or near the middle line M (predetermined breaking points 106), on a crest (predetermined breaking point 107) as well in a connecting member (predetermined breaking point 108).
Figure 2:
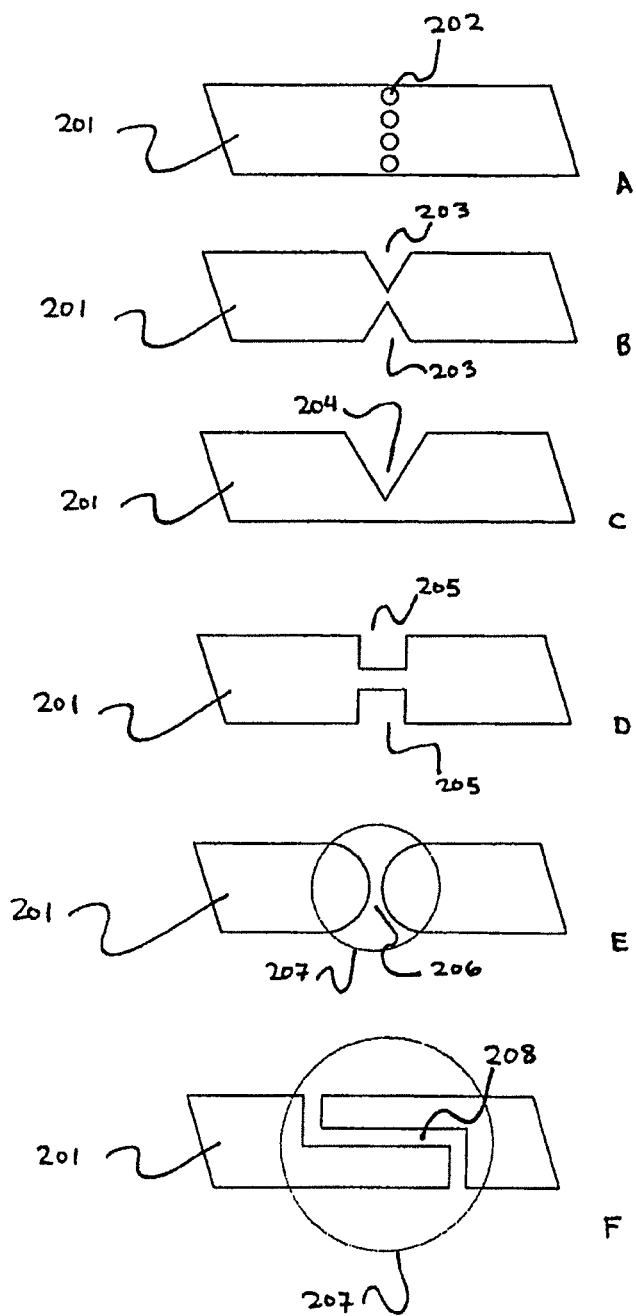
FIG. 2A: A segment (201) of a structural ring or of a connecting member with a predetermined breaking point which is fashioned as a perforation (202).
FIG. 2B: A segment (201) of a structural ring or of a connecting member with a predetermined breaking point which is fashioned as triangular notches (203) disposed above and below.
FIG. 2C: A segment (201) of a structural ring or of a connecting member with a predetermined breaking point which is fashioned as a triangular groove (204) disposed above.
FIG. 2D: A segment (201) of a structural ring or of a connecting member with a predetermined breaking point which is fashioned as rectangular grooves (205) disposed above and below.
FIG. 2E: A segment (201) of a structural ring or of a connecting member with a predetermined breaking point which is fashioned as a rounded cut and which is coated with a polymer (207).
FIG. 2F: A segment (201) of a structural ring or of a connecting member with a predetermined breaking point which is fashioned with a stepwise cut (208) and which is coated with a polymer (207).
FIG. 2G: A cross-section (211) of a structural ring or of a connecting member with a predetermined breaking point which is fashioned as rectangular notches (205) disposed above and below.
FIG. 2H: A cross-section (211) of a structural ring or of a connecting member with a predetermined breaking point which is fashioned as rectangular notches (205) disposed above, below, right and left.
Figure 3:
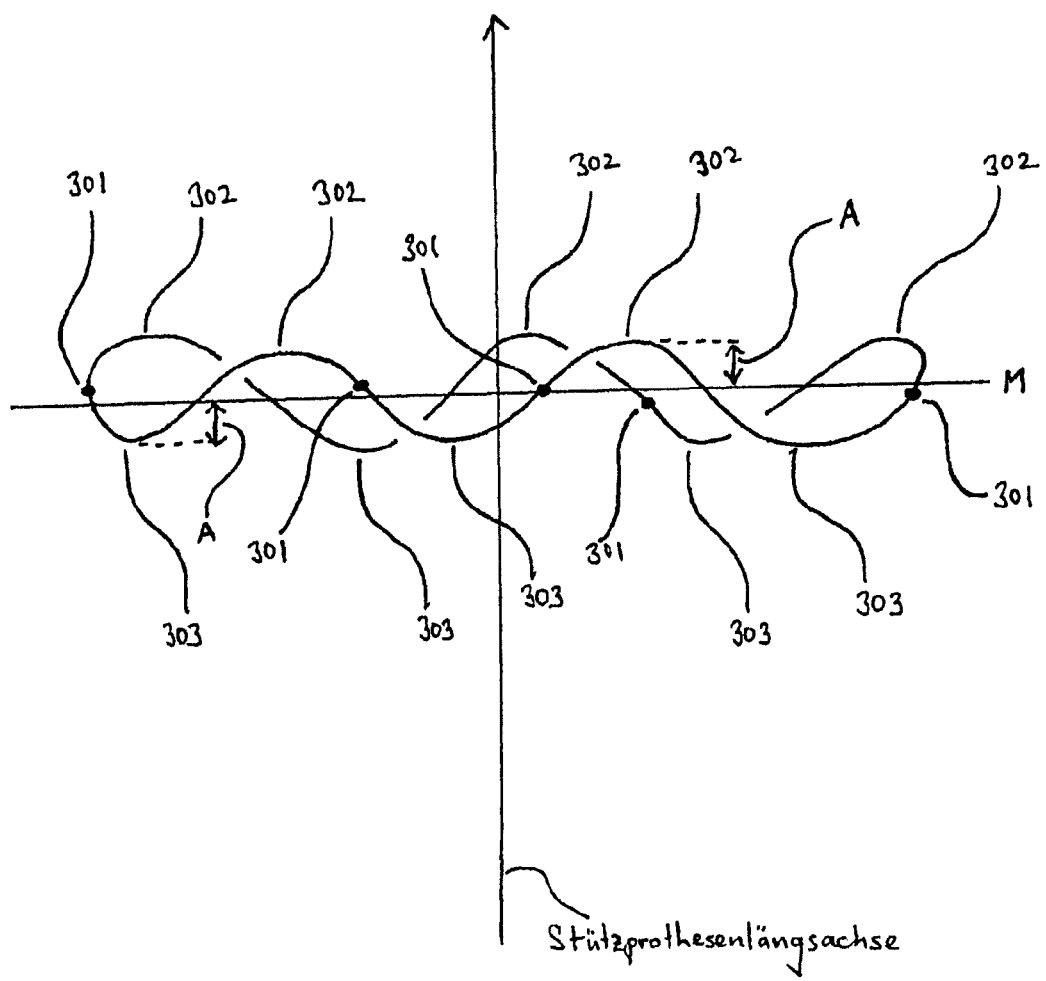
FIG. 3: A perspective view of a structural ring in the terminal regional with sinusoidal shaped deformations. The structural ring shown comprises 5 crests (302), 5 troughs (303) and 5 predetermined breaking points (301) on or near the middle line M running perpendicular to the longitudinal axis of the supporting prosthesis. Amplitude A is also shown. Not shown are connecting members which connect the structural ring shown with a neighboring structural ring in the mesh structure. Also not shown are the elongated connecting members.
Figure 4:
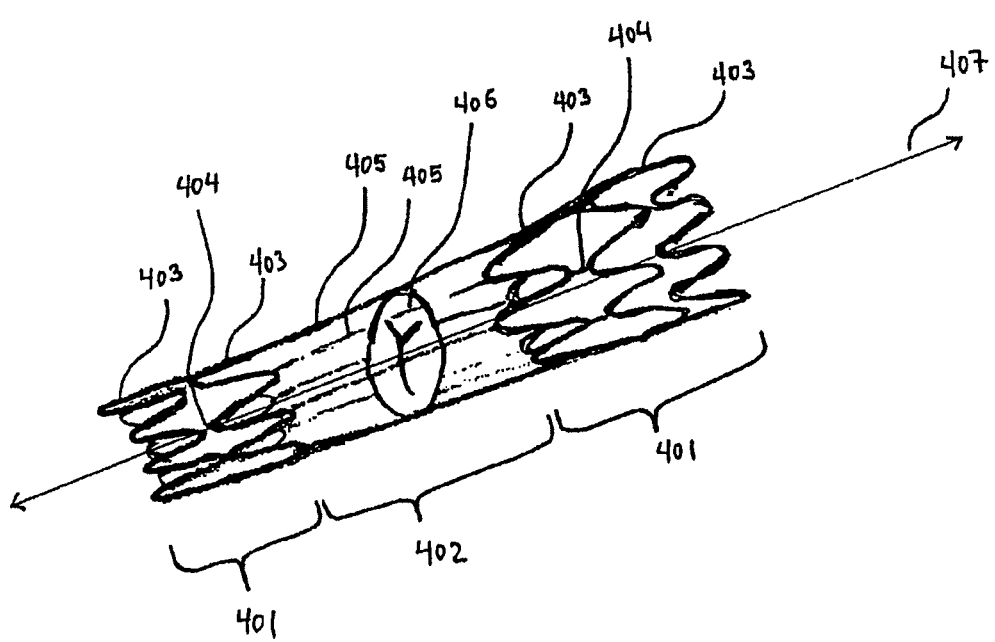
FIG. 4: A perspective view of a TE aortic valve carrying tubular supporting prosthesis according to an embodiment of the invention. The supporting prosthesis shown comprises two terminal regions (401) relative to the longitudinal axis of the supporting prosthesis (407) a middle region (402), elongated connecting members (405) as well as a TE aortic valve (406). Structural rings (403) in their respective terminal regions (401) are connected with one another via connecting members (404).
Figure 5:
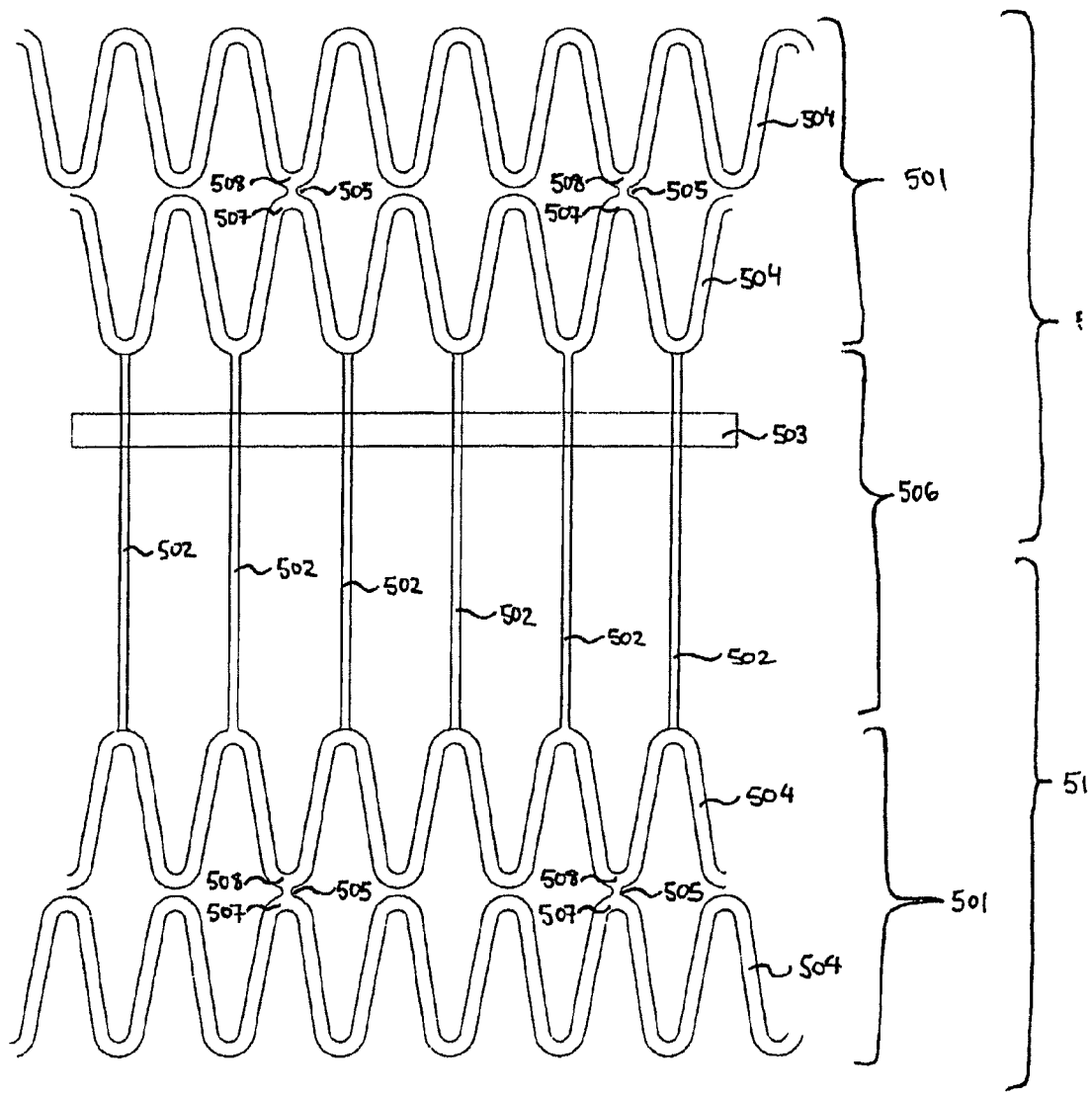
FIG. 5: A plan view of a supporting prosthesis according to an embodiment of the invention. The supporting prosthesis shown comprises two terminal regions (501) relative to the longitudinal axis of the supporting prosthesis and a middle region (506) lying in between. The respective terminal regions are connected with one another via multiple elongated connecting members (502). The two structural rings (504) in each of the two terminal regions are connected with one another via connecting members (505) at their respective crests (507) and troughs (508). Here, the connecting members (505) are fashioned as struts. The TE aortic valve (503) is shown in side view. The entire supporting prosthesis can be divided in two halves along the main axis of the supporting prosthesis. in a distal half (509) which, in the implanted state, lies closer to the heart, and in a proximal half (510) which, in the implanted state, lies further away from the heart. In the embodiment shown, the TE aortic valve (503) is located in the distal half (509) of the supporting prosthesis or in the middle region (506).
Figure 6:
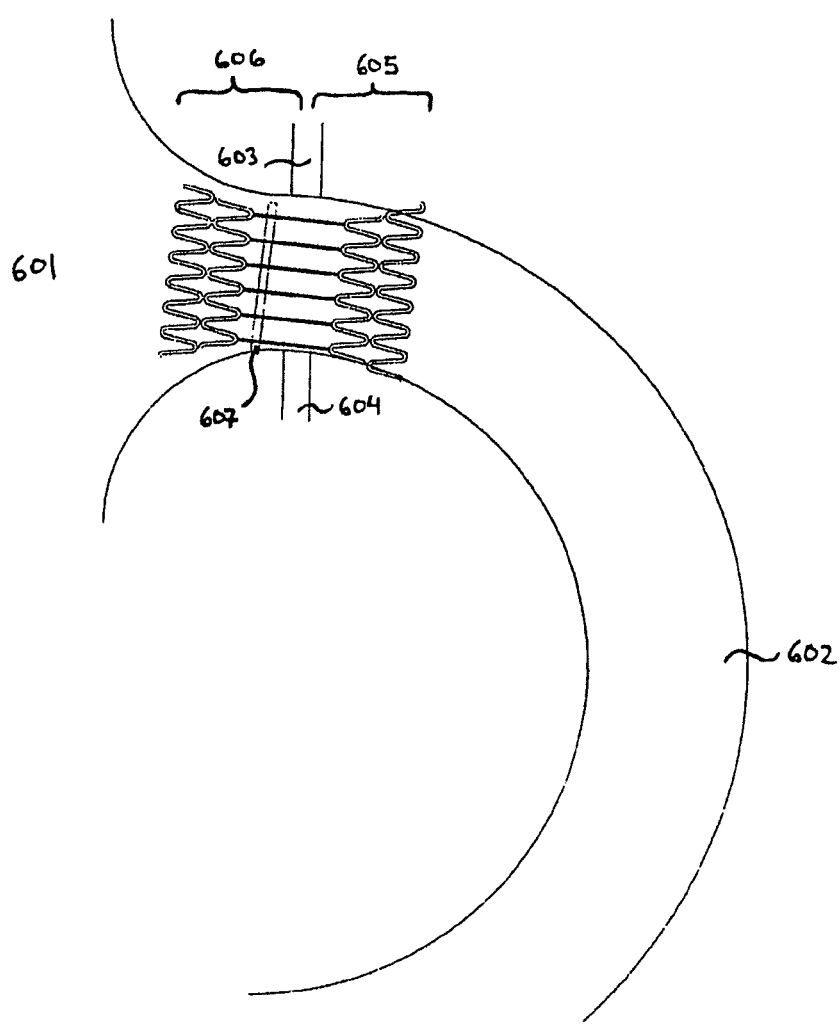
FIG. 6: A schematic view of a supporting prosthesis depicted in FIG. 5 as it may lie in the aorta region following implantation. The supporting prosthesis lies between the heart (601) and the aorta (602) at about the position the aortic valve would normally be located. The left and right coronary vessels (603/604 or 604/603, depending on whether the depicted view is from above or from below) are also shown. The remaining parts of the supporting prosthesis are as depicted and explained in FIG. 5. Only the TE aortic valve (607) in side view as well as the proximal (605) and distal (606) halves of the supporting prosthesis are to be emphasized here. As can be seen, the coronary vessels (603, 604) are not blocked or occluded by the loose middle region of the supporting prosthesis with its elongated connecting members. Nor does the TE aortic valve (607) located in the distal half (606) of the supporting prosthesis disrupt the blood flow through the coronary vessels (603, 604).

In general, the production of a supporting prosthesis capable of growth includes the following method steps:
1. Cutting with a laser
2. Electro-polishing
3. Checking/cleaning
1.1 Cutting with a Laser The supporting prosthesis is manufactured from highly precise material (e.g. 316L, L605, or nitinol) using a solid state laser. In order to freely design the supporting prosthesis, one strives for a method which allows user-defined cutting guidance on a tube. A laser fulfils these requirements in conjunction with a coordinate table, a round axis and a specially manufactured tube guider which precisely guides the tube in the required degrees of freedom under the laser cutting head. The supporting prosthesis structure and the predetermined breaking points, which are in this case mechanical (as for example depicted in FIG. 2) are cut into the tube in a one-step process. The middle part of the supporting prothesis is designed such that the elongated struts cannot damage the valve during implantation. After implantation the struts must securely hold the valve open and may not occlude the coronary arteries (see FIG. 6). After removing the "windows", i.e. the regions which have been cut out, the struts of the supporting prosthesis and thus the finished supporting prosthesis structure remains. This includes not only the structural rings, but also the connecting members connecting these.

1.2 Electro-Polishing

Electro-polishing, generally known to the skilled person, is used to round-off the edges of the supporting prosthesis resulting from the laser cutting in order to minimize damage to the vessel and implantation balloon and to smooth the surface of the supporting prosthesis. An electrochemical polishing method adapted to the special requirements of supporting prosthesis production is used. The adaptation for the processing of supporting prostheses mainly includes a polishing apparatus which ensures a uniform current flow during the polishing process. During this, the supporting prostheses are continually moved in the electro-polishing bath and are simultaneously put under voltage.

1.3 Checking/Cleaning

After the polishing by the electro-polishing method described above, the supporting prosthesis are cleaned of polishing residues by etching and multiple rinses and are optically checked as well as measured and packaged. In the optical check, the entire surface is assessed. Here, supporting prostheses which i.a. do not fulfil the following criteria, are rejected:

uniform, smooth surface
continuous rounding of edges without points.

1.4 Connection Valve—Prosthesis

TE heart valves can be prepared according to known methods, above all by using homologous or autologous human cells (see e.g. EP 1499366). The TE valve prepared in this way must be connected with the supporting prosthesis without damaging it. The chosen manner of connection must work with the connecting struts of the supporting prosthesis in such a manner as to ensure a reliable crimping of the supporting prosthesis as well as a leak-free implantation of the valve. One may choose from mechanical means of connections such as sewing, clamping, gluing or bonding, in which the individual connecting struts are connected with the valve. Alternatively, a decellularized TE heart valve or a polymer structure for a heart valve which has not yet decellularized may first be integrated into or attached to a supporting prosthesis and only then populated with homologous or autologous cells according to known methods.

The invention claimed is:

1. A tubular supporting prosthesis comprising:
   two terminal regions relative to the longitudinal axis of the supporting prosthesis and a middle region disposed between the two terminal regions,
   wherein each of said terminal regions comprises a mesh structure made of at least two structural rings which are connected to one another via connecting members and are disposed point symmetrically about the longitudinal axis of the supporting prosthesis,
   wherein the middle region is formed by elongated connecting members which are connected with each of the structural rings disposed closest to the middle point of the longitudinal axis of the supporting prosthesis,
   wherein an aortic valve produced by means of tissue engineering is fixed and/or integrated into the middle region, and
   wherein at least one of the structural ring and connecting members comprise at least one predetermined breaking point which comprises multiple layers of different biologically degradable materials, wherein the multiple layers of different biologically degradable materials are located only at the predetermined breaking point area, such that the rate of dissolution of the predetermined breaking point proceeds in a chronologically graduated manner.

2. The supporting prosthesis according to claim 1, wherein at least one structural ring of the mesh region comprises n periodic deformations extending along the longitudinal axis of the supporting prosthesis and forming crests and troughs, said deformations comprising an amplitude A relative to the longitudinal axis of the supporting prosthesis,
   wherein n=16-70.

3. The supporting prosthesis according to claim 2, wherein the deformations are sinusoidal, rectangular, saw-tooth or triangular shaped.

4. The supporting prosthesis according to claim 2, wherein the number of the periodic deformations of two respectively neighboring structural rings is identical or differs from one another by at least one whole number.

5. The supporting prosthesis according to claim 2, wherein two neighboring structural rings are phase-shifted to one another such that crests of one structural ring are connected with troughs of a respectively neighboring structural ring via the connecting members.

6. The supporting prosthesis according to claim 1, wherein the connecting members are fashioned as rings, clamps, loops, threads, wires or struts, said loops, threads, wires or struts extending parallel to the longitudinal axis of the supporting prosthesis.

7. The supporting prosthesis according to claim 1, wherein the structural rings and/or the connecting members consist at least in part of a biologically degradable material.

8. The supporting prosthesis according to claim 7, wherein the biologically degradable material is chosen from at least one alloy, at least one polymer or at least one stainless steel with shape memory.

9. The supporting prosthesis according to claim 8, wherein the alloy with shape memory is a nickel-titanium alloy, an aluminium alloy, a magnesium alloy or an iron alloy.

10. The supporting prosthesis according to claim 7, wherein the biologically degradable material is a polymer selected from the group of polyglycolic acid (PGA), polylactic acid (PLA), polyhydroxyalkanoate (PHA), poly-4-hydroxybutyrate (P4HB), polycaprylactones (PLGA), polycarbonates, polyamides, polyanhydrides, polyamino acids, polyorthoesters, polyacetates, polycyanoacrylates as well as degradable polyurethanes and non-erodible polymers such as polyacrylates, ethylenvinylacetate polymers, other substituted cellulose acetates as well as derivatives thereof, polyesters of the hydroxycarboxy acids, polyanhydrides of the dicarboxyesters, copolymers of the hydroxycarboxy acids and of the dicarboxyesters, a synthetic polymer of at least one glycolide, lactide, p-dioxanone, caprylactone, trimethylenecarbonate and/or butyrolactone, polymers or copolymers of glycolic acid, lactic acid and sebacic acid, polyhydroxyalkanoate compositions of 2-, 3-, 4- or 5-hydroxy acids, e.g. poly-4-hydroxybutyrates, a poly-4-hydroxybutyrate-co-3-hydroxbutyrate, homopolymers and copolymers with any desirable combination of 3-hydroxybutyrates, 3-hydroxyvalerate, 3-hydroxyproprionate, 2-hydroxybutyrate, 4-hydroxybutyrate, 4-hydroxyvalerate, 3-hydroxyhexanoate, 3-hydroxyheptanoate, 3-hydroxyoctanoate, 3-hydroxynonanoate, 3-hydroxytridecanoate, 3-hydroxytetradecanoate, 3-hydroxypentadecanoate, 3-hydroxyhexadecanoate, 3-hydroxyheptadecanoate and 3-hydroxyoctadecanoate or a combination thereof.

11. The supporting prosthesis according to claim 1, wherein the at least one predetermined breaking point in the structural ring is disposed on or next to the middle point between the crest and the trough of the periodically deformed structural ring.

12. The supporting prosthesis according to claim 1, wherein the at least one predetermined breaking point is made of one non-metallic material.

13. The supporting prosthesis according to claim 2, wherein the length of the elongated connecting members is 0.75-3-fold of the amplitude A.

14. The supporting prosthesis according to claim 11, wherein the at least one predetermined breaking point is fashioned such that it can be forced apart, dissolved or weakened by external influence.

15. The supporting prosthesis according to claim 14, wherein the external influence is chosen from: sound waves; at least one magnetic field; a combination of magnetic field and electromagnetic field; electromagnetic radiation; electrical energy and any desired combination thereof.

16. The supporting prosthesis according to claim 15, wherein the sound waves are ultrasound and/or shock waves.

17. The supporting prosthesis according to claim 14, wherein the external influence is magnetic resonance imaging (MRI).

18. The supporting prosthesis according to claim 14, wherein the external influence is X-ray radiation or infrared radiation (thermal energy).

19. The supporting prosthesis according to claim 14, wherein the external influence is applied from inside or outside of the body.

20. The supporting prosthesis according to claim 19, wherein the external influence is applied from the outside of the body with the help of an intravascular catheter or in a minimally invasive manner with the help of endoscopy.

21. The supporting prosthesis according to claim 7, wherein the biologically degradable material is a polymer with shape memory selected from the group of tert-butylacrylate, poly(ethyleneglycol)dimethacrylate and PCL combined with 2,4-toluenediisocyanate ethyleneglycol.

22. The supporting prosthesis according to claim 2, wherein n=20-56.

23. The supporting prosthesis according to claim 2, wherein n=24-42.

24. The supporting prosthesis according to claim 13, wherein the length of the elongated connecting members is 1-2 fold of the amplitude A.

25. The supporting prosthesis according to claim 1, wherein the structural ring and connecting members comprise at least one predetermined breaking point.

26. A tubular supporting prosthesis comprising:
   two terminal regions relative to the longitudinal axis of the supporting prosthesis and a middle region disposed between the two terminal regions,
   wherein each of said terminal regions comprises a mesh structure made of at least two structural rings which are connected to one another via connecting members and are disposed point symmetrically about the longitudinal axis of the supporting prosthesis,
   wherein the middle region is formed by elongated connecting members which are connected with each of the structural rings disposed closest to the middle point of the longitudinal axis of the supporting prosthesis,
   wherein an aortic valve produced by means of tissue engineering is fixed and/or integrated into the middle region, and
   wherein at least one of the structural ring and connecting members comprise at least one predetermined breaking point which comprises multiple layers of different biologically degradable materials, wherein at least one of the multiple layers of different biologically degradable materials, the multiple layers of different biologically degradable materials being located only at the predetermined breaking point, has a different rate of dissolution than one or more of the other multiple layers at the predetermined breaking point, such that the rate of dissolution of the predetermined breaking point proceeds in a chronologically graduated manner.

27. A tubular supporting prosthesis according to claim 1 or claim 26, wherein the prosthesis is coated with one or more biologically degradable materials, or one or more non-biologically degradable materials.

* * * * *

UNITED STATES PATENT AND TRADEMARK OFFICE
CERTIFICATE OF CORRECTION

PATENT NO. : 8,617,237 B2  
APPLICATION NO. : 12/527138  
DATED : December 31, 2013  
INVENTOR(S) : Simon P. Hoerstrup et al.

Page 1 of 1

It is certified that error appears in the above-identified patent and that said Letters Patent is hereby corrected as shown below:

Title Page: Item 75

The first Inventor's city of residence is currently listed as

Schweiz

To be deleted: Schweiz

To be replaced by: Zurich

The second Inventor's city of residence is currently listed as

Schweiz

To be deleted: Schweiz

To be replaced by: Herrliberg

Signed and Sealed this  
Eighteenth Day of March, 2014

Michelle K. Lee  
*Deputy Director of the United States Patent and Trademark Office*